United States Patent [19]
Wachtel et al.

[11] Patent Number: 6,117,895
[45] Date of Patent: *Sep. 12, 2000

[54] PHARMACEUTICAL PREPARATIONS FOR TNF INHIBITION

[75] Inventors: Helmut Wachtel; Hermann Graf; Herbert Schneider, all of Berlin, Germany; Daryl Faulds, Mill Valley, Calif.; H. Daniel Perez, Kentfield, Calif.; Harald Dinter, San Rafael, Calif.

[73] Assignee: Schering Aktiengesellschaft, Berlin, Germany

[ * ] Notice: This patent issued on a continued prosecution application filed under 37 CFR 1.53(d), and is subject to the twenty year patent term provisions of 35 U.S.C. 154(a)(2).

This patent is subject to a terminal disclaimer.

[21] Appl. No.: 08/683,467

[22] Filed: Jul. 18, 1996

Related U.S. Application Data

[63] Continuation of application No. 08/598,844, Feb. 9, 1996, abandoned.

[30] Foreign Application Priority Data

Feb. 10, 1995 [DE] Germany .................. 195 05 516

[51] Int. Cl.⁷ .................................................. A61K 31/42
[52] U.S. Cl. ............................................ 514/376; 514/380
[58] Field of Search ...................... 514/380, 376

[56] References Cited

U.S. PATENT DOCUMENTS

| | | | |
|---|---|---|---|
| 4,012,495 | 3/1977 | Schmiechen et al. | 424/274 |
| 4,153,713 | 5/1979 | Huth et al. | 424/274 |
| 4,186,129 | 1/1980 | Huth et al. | 548/186 |
| 4,208,406 | 6/1980 | Lapinet et al. | 424/180 |
| 4,824,838 | 4/1989 | Wachtel et al. | 514/380 |
| 5,227,369 | 7/1993 | Rosen et al. | 514/23 |
| 5,420,154 | 5/1995 | Christensen, IV et al. | 514/424 |
| 5,541,219 | 7/1996 | Fenton et al. | 514/532 |
| 5,672,622 | 9/1997 | Hedgepeth et al. | 514/422 |
| 5,783,591 | 7/1998 | Klose et al. | 514/376 |

FOREIGN PATENT DOCUMENTS

| | | |
|---|---|---|
| 0411754 A2 | 2/1991 | European Pat. Off. . |
| 0411754 A3 | 2/1991 | European Pat. Off. . |
| 92/02220 | 2/1992 | WIPO . |
| 92/19594 | 11/1992 | WIPO . |
| 93/16706 | 9/1993 | WIPO . |
| 93/19068 | 9/1993 | WIPO . |

OTHER PUBLICATIONS

Strieter et al., *Biochem. Biophys. Res. Comm.*, 155:1230–1236 (1988).
Taffet et al., *Cell. Immunol.*, 120:291–300 (1989).
Spengler et al., *Infec. Immun.*, 57:2837–2841 (1989).
Reeves et al., *Biochem. J.*, 241:535–541 (1987).
Tracey et al., *Nature*, 330:662–664 (1987).
Old, *Nature*, 330:602–603 (1987).
Millar et al., *Lancet*, pp. 712–713 (1989).
Dezube et al., *Lancet*, pp. 662–663 (1990).
Perchellet et al., *Cancer Letters*, 29:127–137 (1985).
Perchellet et al., *Carcinogenesis*, 3(10):1149–1158 (1982).
Tonelli et al., *Endocrinology*, 77:625–634 (Oct. 1965).
Seely et al., *Proceedings of the Society for Experimental Biology and Medicine*, 159:223–225 (1978).
Jaiswal et al., *Journal of Heterocyclic Chemistry*, 15(3):519–521 (May 1978).
Schmiechen et al. (1990) *Psychopharmacology*, 102, pp. 17–20.
Strieter et al. (1988) *Biochem. and Biophys. Research Comm.* 155(3), pp. 1230–1236.
Taffet et al. (1989) *Cell. Immunology* 120, pp. 291–300.
Spengler et al. (1989) *Infection and Immunity*, 57(9), pp. 2837–2841.
Reeves et al. (1997) *Biochem.J.*, 241, pp. 535–541.
Tracey et al. (1987) Nature, 330, pp. 662–664.
L.J. Old (1987) *Nature*, pp. 602–603.
Millar et al. *The Lancet* (1989) No. 8665, pp. 712–713.
DeZube et al., The Lancet (1989) No. 8690, pp. 662–663.
Molnar–Kimber (1992) *Mediators of Inflammation*, 1, pp. 411–417.
Schmiechen et al. (1990) *Psychopharmacology*, 102, pp. 17–20.
Molnar–Kimber et al. (1992) Mediators of Inflammation 1, 411–417.
Nicholson et al. (1991) *Tips*, vol. 12, (9 pages total).
Dent et al. (1990) Br. J. Pharm., vol. 22, p. 163.
Wyngaarden et al. (1992) XXIII Neurology, *The Demyelinating Diseases*, pp. 2219–2200.
Nataf et al. (1993) Acta Neurol Scand., 88: pp. 97–99.
Rott et al. (1993) Eur. J. Immunol. 23: pp. 1745–1751.
Schade et al. (1993) Eur. J. Pharm. 230: pp. 9–14.
Frohlich et al. (1988) J. Invest. Dermatolgy, 90: p. 240.
Adams et al. (1993) Principles of Neurology (5th Ed.) pp. 776–792.
Sharief et al. (1991) N.E. Jour. Med. 325(7), pp. 467–472.

(List continued on next page.)

*Primary Examiner*—Theodore J. Criares
*Attorney, Agent, or Firm*—Millen, White, Zelano & Branigan

[57] ABSTRACT

Compounds of formula I

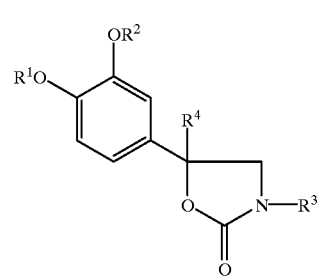

are useful for treating TNF-mediated diseases.

39 Claims, No Drawings

OTHER PUBLICATIONS

Rentz et al. (1998) The J. of Immun., 141(7), pp. 2388–2393.
Benvenuto et al., J. of Neurology (1990) Supp 1 to vol. 237, pp. S83.
Kirby et al. (Aug. 30, 1980) The Lancet, pp. 453–454.
Renz et al. (1988) The Jour. of Immun., vol. 141 (7), pp. 2386–2393.
Marivet et al. (1989) J. Med. Chem., 32(7), pp. 1450–1457.

PHARMACEUTICAL PREPARATIONS FOR TNF INHIBITION

This application is a continuation application of U.S. Ser. No. 08/598,844, filed on Feb. 9, 1996, now abandoned.

This invention relates to the use of the compounds of formula I for the production of pharmaceutical agents for treating diseases that are mediated by activation of the tumor necrosis factor (TNF).

The compounds of formula I are described in, for example, U.S. Pat. No. 4,186,129 and WO 8602268. It is known from these patents that the compounds of formula I have phosphodiesterase-inhibiting action, exhibit central-depressive, anti-dopaminergic, antinociceptive, and anticonvulsive action, and are suitable for topical treatment of inflammations. It is further known from U.S. Pat. No. 4,824,838 that compounds of formula I can be used as antidepressants.

SUMMARY OF THE INVENTION

It has now been found that the compounds of formula I inhibit TNF production and therefore can be used for treating diseases that are mediated by the activation of TNF.

Suitable according to the invention are the racemic and optically active compounds of formula I

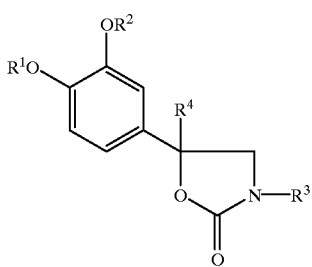

in which
- $R^1$ means $C_{1-4}$ alkyl,
- $R^2$ means $C_{1-6}$ alkyl, $C_{3-7}$ cycloalkyl, $C_{3-7}$ cycloalkyl-$C_{1-2}$ alkyl, $C_{2-6}$ alkenyl, $C_{3-7}$ alkynyl, a heterocycle or $C_{1-6}$ alkyl, which is substituted with one or more of halogen, hydroxy, carboxy, $C_{1-4}$ alkoxy, $C_{1-4}$ alkoxycarbonyl, or an amino group that is optionally substituted with $C_{1-4}$ alkyl,
- $R^3$ means hydrogen, $C_{1-6}$ alkyl, acyl, aryl, aralkyl, or aryl substituted with 1 or 2 methyl groups and
- $R^4$ means hydrogen or $C_{1-6}$ alkyl.

The compounds of formula I can contain one or more chiral centers and also comprise racemic diastereomer mixtures as well as individual optical isomers.

In each case, alkyl means straight-chain or branched alkyl groups, such as, for example, methyl, ethyl, n-propyl, isopropyl, n-butyl, sec-butyl, isobutyl, tert-butyl, pentyl, 2-methyl-butyl, 2,2-dimethylpropyl and hexyl. Alkyl radicals with 1–4 carbon atoms are preferred.

Alkenyl means, for example, 1-propenyl, 2-propenyl or 3-methyl-2-propenyl and alkynyl, for example, propargyl.

Cycloalkyl means, for example, cyclopropyl, cyclobutyl, cyclopentyl, cyclohexyl or cycloheptyl, especially $C_{3-5}$ cycloalkyls.

In each case, aryl or aralkyl means an aromatic ring or an aromatic ring system with 6 to 10 carbon atoms, such as, for example, phenyl, benzyl, phenethyl, or naphthyl. A monocyclic form is preferred.

Acyl means aliphatic and aromatic carboxylic acids, such as, for example, $C_{1-6}$ alkanoyl, benzoyl, etc., e.g., wherein the aromatic groups are as defined above for aryl and aralkyl.

The term "heterocycle" comprises a 5- or 6-membered saturated heterocycle with an oxygen, sulfur or nitrogen atom, such as, for example, 2- or 3-tetrahydropyranyl, 2- or 3-tetrahydrofuranyl, 2- or 3-tetrahydrothienyl, dihydropyranyl, pyrrolidinyl, pyrrolinyl, piperidinyl as well as N-alkyl-pyrrolidinyl and N-alkyl-piperidinyl, in which the alkyl radical contains 1–4 carbon atoms, preferably tetrahydrofuranyl.

Halogen means chlorine, fluorine, bromine, and iodine.

According to the invention, the compounds of formula I in which $R^1$ means methyl and $R^3$ means hydrogen are preferred. Especially suitable are compounds in which $R^4$ means hydrogen or methyl and $R^2$ means alkyl or cycloalkyl, whereby $R^4$ in the meaning of $CH_3$ is especially preferred.

The production of the compounds of formula I, their isomers and their mixtures is carried out according to methods known in the art, which are described in, for example, the prior art mentioned above. See especially U.S. application Ser. No. 06/027,480 filed on even date, for preparation of chiral compounds. The latter is incorporated by reference herein entirely, including its pharmacological aspects.

Diseases that are mediated by TNF are defined both as diseases that are triggered by the production of TNF and diseases in which other cytokines, such as, for example, Il-1 or Il-6, are altered by TNF.

TNF is defined both as TNF-α and TNF-β, which are both antagonized by the compounds of formula I. Preferably, TNF-α is inhibited.

The compounds of formula I are therefore suitable for the production of a pharmaceutical preparation that is used for the treatment and prophylaxis of diseases in living creatures, which are triggered by stimulation of TNF. Diseases that are altered by excessive or unregulated TNF stimulation include, for example, allergic and inflammatory diseases, auto-immune diseases, pulmonary diseases, infectious diseases and bone resorption diseases, such as rheumatoid arthritis, rheumatoid spondylitis, osteo-arthritis, gout, sepsis, septic shock, endotoxin shock, gramnegative sepsis, toxic shock syndrome, ARDS (acute respiratory distress syndrome), pulmonary sarcoidosis, asthma, silicosis, cachexia, ulcerative colitis, Crohn's disease, osteoporosis, organic lesions after reperfusion, inflammatory diseases of the central nervous system such as cerebral malaria, multiple sclerosis, panencephalitis, infectious diseases such as AIDS, bovine insanity, inflammatory diseases of the skin such as urticaria, psoriasis, atopic dermatitis, contact dermatitis, lupus erythematosus as well as diabetes insipidus, neuroprotection, e.g., in the case of Parkinson's disease, dementia, for example, after multiple infarctions and stroke.

The effectiveness of the compounds of formula I in the above-mentioned indications can be shown by appropriate, commonly used pharmacological tests.

The agents are produced according to the usual processes, by the active ingredient being put into the form of a pharmaceutical preparation that is suitable for enteral or parenteral administration, with suitable vehicles, adjuvants and/or additives. The preparations thus obtained can be used as pharmaceutical agents in human or veterinary medicine. Administration can be done orally or sublingually as a solid in the form of capsules or tablets or as a liquid in the form of solutions, suspensions, elixirs, aerosols, or emulsions, or rectally in the form of suppositories, or in the form of injection solutions that can optionally also be administered subcutaneously, intramuscularly or intravenously, or topically, or intrathecally. As adjuvants for the desired pharmaceutical agent formulation, inert organic and inorganic media that are known to one skilled in the art, such as, e.g., water, gelatin, gum arabic, lactose, starch, magnesium stearate, talc, vegetable oils, polyalkyleneglycols, etc., are suitable. Moreover, preservatives, stabilizers, wetting agents, emulsifiers, or salts can optionally be contained to alter the osmotic pressure or buffer.

The pharmaceutical preparations can be present in solid form, for example, as tablets, coated tablets, suppositories, capsules or in liquid form, e.g., as solutions, suspensions or emulsions.

As vehicle systems, near-interface adjuvants such as salts, bile acids, or animal or plant phospholipids and mixtures of them, as well as liposomes or their components can also be used.

For oral administration, especially tablets, coated tablets or capsules with talc and/or hydrocarbon vehicles or binders, such as, e.g., lactose, corn or potato starch, are especially suitable. Application can also be done in liquid form, such as, e.g., in the form of juice, to which sweetener is optionally added.

The compounds of formula I are used in dosages that are sufficient to reduce TNF production to normal levels or below.

The dosage of the active ingredients can vary depending on the method of administration, the age and weight of the patient, the type and severity of the disease to be treated, and similar factors. The daily dose for an adult human is 0.5–50 mg, preferably 0.1–5 mg, whereby the dose can be given as a single dose to be administered one time or divided into 2 or more daily doses. The compounds can be used analogously to those described in U.S. Ser. No. 327,478 of Oct. 21, 1994, and U.S. Ser. No. 284,527 of Jul. 28, 1994.

The effectiveness of the compounds according to the invention can be demonstrated in, for example, conventional protocols using a model based on animals that suffer from experimental allergic encephalomyelitis (EAE), a disease of the central nervous system that is caused by T-lymphocytes. The disease can be triggered in rodents and primates by immunization and histopathologically and symptomatically resembles pathologic conditions in humans. The course of the disease can be monitored with the aid of nuclear spin tomography.

Macrophages and microglia cells, which perform macrophage functions in the brain, mediate the release of TNF-α during experimental allergic encephalomyelitis (EAE). If macrophages are stimulated, for example, by lipopolysaccharide (LPS), a secretion of TNF-α is carried out in vitro and in vivo within hours.

A murine macrophage cell line (RAW 264) was preincubated for 30 minutes in the presence and in the absence of various concentrations of PDE-IV inhibitors and then stimulated with LPS (10 ng/ml). 18 hours after stimulation, the culture medium was removed, and the TNF-α release was measured with a specific Elisa test. The test can be obtained from various companies, i.a., from the British biotechnology company Genzyme, and it is carried out as the manufacturer describes.

5-(3-propoxy-4-methoxyphenyl)-5-methyl-2-oxazolidinone inhibited the LPS-induced TNF-α release by such RAW cells with $IC_{50}=0.50$ ($\mu$M).

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire disclosure of all applications, patents and publications, cited above and below, and of corresponding German application P 195 05 516.0 filed Feb. 10, 1995, are hereby incorporated by reference.

Test Systems:

Number of Specific Lymphocytes:

In this case, the proliferation of lymphocytes, which specifically react, on the one hand, against MBP (myelin basic protein) and, on the other hand, against PLP (proteolipid protein), is studied against pathogenic germs, auto-antigens and viral antigens. This is measured by the incorporation of radiolabeled thymidine. Such measurements are described in the publication by E. BERAUD et al. (1993) Neuroimmunol 47: 41–53 and in the publication by C. M. PELFREY et al. (1993) Neuroimmunol 46: 33–42. Also, Amitabh GAUR et al. (1992) Science 258: 1941 provides a good presentation of these measuring methods.

ELISA for TNF Concentration, Bioassay for TNF

[ELISA=Enzyme-Linked Immunosorbent Assay]

The test can be obtained from various companies, i.a., from the British biotechnology company Genzyme, and is carried out as the manufacturer describes.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A method of treating a disease mediated by activation of the tumor necrosis factor, comprising administering to a patient in need of such treatment an amount effective to inhibit TNF or its production of an optically active or racemic compound of formula

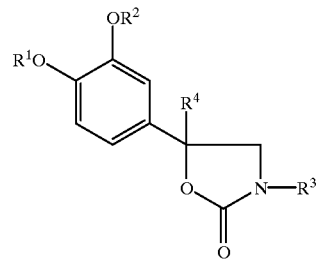

I in which $R^1$ is $C_{1-4}$ alkyl, $R^2$ is $C_{1-6}$ alkyl, $C_{3-7}$ cycloalkyl, $C_{3-7}$ cycloalkyl-$C_{1-2}$ alkyl, $C_{2-6}$ alkenyl, $C_{3-7}$ alkynyl, a 5- or 6-membered, saturated heterocycle, or a $C_{1-6}$ alkyl substituted with one or more of halogen, hydroxy, carboxy, $C_{1-4}$ alkoxy, $C_{1-4}$ alkoxy-carbonyl or an amino group that is optionally substituted with $C_{1-4}$ alkyl, $R^3$ is hydrogen, $C_{1-6}$ alkyl, acyl, $C_{6-10}$-aryl, $C_{6-10}$-aralkyl, or $C_{6-10}$-aryl substituted with 1 or 2 methyl groups and $R^4$ is hydrogen or $C_{1-6}$ alkyl, with the proviso that said compound is not administered locally to treat inflammation.

2. A method of claim 1, wherein said compound is 5-(3-cyclopentyloxy-4-methoxyphenyl)-5-methyl-2-oxazolidinone.

3. A method of claim 1, wherein said compound is 5-(3-propoxy-4-methoxyphenyl)-5-methyl-2-oxazolidinone.

4. A method according to claim 1 for treating an inflammatory disease of the central nervous system.

5. A method according to claim 1 for treating an infectious disease.

6. A method according to claim 1 for treating a bone resorption disease.

7. A method according to claim 1 for treating a pulmonary disease.

8. A method according to claim 1 for treating an auto-immune disease.

9. A method of treating multiple sclerosis comprising administering an optically active or racemic compound of formula I

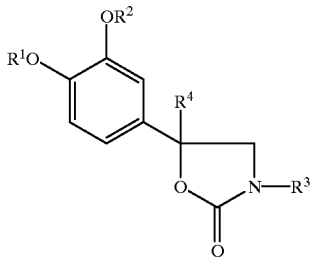

in which $R^1$ is $C_{1-4}$ alkyl, $R^2$ is $C_{1-6}$ alkyl, $C_{3-7}$ cycloalkyl, $C_{3-7}$ cycloalkyl-$C_{1-2}$ alkyl, $C_{2-6}$, alkenyl, $C_{3-7}$ alkynyl, a 5- or 6-membered, saturated heterocycle, or a $C_{1-6}$ alkyl substituted with one or more of halogen, hydroxy, carboxy, $C_{1-4}$ alkoxy, $C_{1-4}$ alkoxy-carbonyl or an amino group that is optionally substituted with $C_{1-4}$ alkyl, $R^3$ is hydrogen, $C_{1-6}$ alkyl, acyl, $C_{6-10}$-aryl, $C_{6-10}$-aralkyl, or $C_{6-10}$-aryl substituted with 1 or 2 methyl groups and $R^4$ is hydrogen or $C_{1-6}$ alkyl.

10. A method of claim 9, wherein said compound is 5-(3-cyclopentyloxy-4-methoxyphenyl)-5-methyl-2-oxazolidinone.

11. A method of claim 9, wherein said compound is 5-(3-propoxy-4-methoxyphenyl)-5-methyl-2-oxazolidinone.

12. A method of claim 9, wherein $R^1$ is $CH_3$ and $R^3$ is H.

13. A method of claim 9, wherein $R^4$ is $CH_3$ or H and $R^2$ is alkyl or cycloalkyl.

14. The method of claim 1, wherein said compound of formula I is optically active.

15. A method of claim 14, wherein said compound is 5-(3-cyclopentyloxy-4-methoxyphenyl)-5-methyl-2-oxazolidinone.

16. A method of claim 14, wherein said compound is 5-(3-propoxy-4-methoxyphenyl)-5-methyl-2-oxazolidinone.

17. A method according to claim 14 for treating an inflammatory disease of the central nervous system.

18. A method according to claim 14 for treating an infectious disease.

19. A method according to claim 14 for treating a bone resorption disease.

20. A method according to claim 14 for treating a pulmonary disease.

21. A method according to claim 14 for treating an auto-immune disease.

22. A method of treating multiple sclerosis comprising administering an optically active compound of formula I

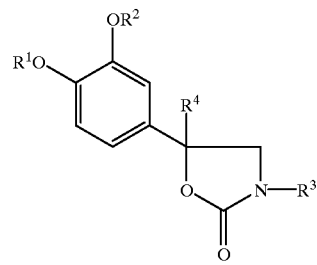

in which $R^1$ is $C_{1-4}$ alkyl, $R^2$ is $C_{1-16}$ alkyl, $C_{3-7}$ cycloalkyl, $C_{3-7}$ cycloalkyl-$C_{1-2}$ alkyl, $C_{2-6}$ alkenyl, $C_{3-7}$ alkynyl, a 5- or 6-membered, saturated heterocycle, or a $C_{1-16}$ alkyl substituted with one or more of halogen, hydroxy, carboxy, $C_{1-14}$ alkoxy, $C_{1-14}$ alkoxy-carbonyl or an amino group that is optionally substituted with $C_{1-14}$ alkyl, $R^3$ is hydrogen, $C_{1-16}$ alkyl, acyl, $C_{6-10}$-aryl, $C_{6-10}$-aralkyl, or $C_{6-10}$-aryl substituted with 1 or 2 methyl groups and $R^4$ is hydrogen or $C_{1-16}$ alkyl.

23. A method of claim 22, wherein said compound is 5-(3-cyclopentyloxy-4-methoxyphenyl)-5-methyl-2-oxazolidinone.

24. A method of claim 22, wherein said compound is 5-(3-propoxy-4-methoxyphenyl)-5-methyl-2-oxazolidinone.

25. A method of claim 22, wherein $R^1$ is $CH_3$ and $R^3$ is H.

26. A method of claim 22, wherein $R^4$ is $CH_3$ or H and $R^2$ is alkyl or cycloalkyl.

27. The method of claim 1, wherein said compound of formula I is racemic.

28. A method of claim 27, wherein said compound is 5-(3-cyclopentyloxy-4-methoxyphenyl)-5-methyl-2-oxazolidinone.

29. A method of claim 28, wherein said compound is 5-(3-propoxy-4-methoxyphenyl)-5-methyl-2-oxazolidinone.

30. A method according to claim 29 for treating an inflammatory disease of the central nervous system.

31. A method according to claim 27 for treating an infectious disease.

32. A method according to claim 27 for treating a bone resorption disease.

33. A method according to claim 27 for treating a pulmonary disease.

34. A method according to claim 27 for treating an auto-immune disease.

35. A method of treating multiple sclerosis comprising administering a racemic compound of formula I

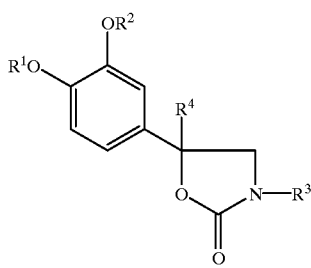

in which
- $R^1$ is $C_{1-4}$ alkyl,
- $R^2$ is $C_{1-16}$ alkyl, $C_{3-7}$ cycloalkyl, $C_{3-7}$ cycloalkyl-$C_{1-2}$ alkyl, $C_{2-6}$ alkenyl, $C_{3-7}$ alkynyl, a 5- or 6-membered, saturated heterocycle, or a $C_{1-16}$ alkyl substituted with one or more of halogen, hydroxy, carboxy, $C_{1-14}$ alkoxy, $C_{1-14}$ alkoxy-carbonyl or an amino group that is optionally substituted with $C_{1-14}$ alkyl,
- $R^3$ is hydrogen, $C_{1-16}$ alkyl, acyl, $C_{6-10}$-aryl, $C_{6-10}$-aralkyl, or $C_{6-10}$-aryl substituted with 1 or 2 methyl groups and
- $R^4$ is hydrogen or $C_{1-16}$ alkyl.

36. A method of claim 35, wherein said compound is 5-(3-cyclopentyloxy-4-methoxyphenyl)-5-methyl-2-oxazolidinone.

37. A method of claim 35, wherein said compound is 5-(3-propoxy-4-methoxyphenyl)-5-methyl-2-oxazolidinone.

38. A method of claim 35, wherein $R^1$ is $CH_3$ and $R^3$ is H.

39. A method of claim 35, wherein $R^4$ is $CH_3$ or H and $R^2$ is alkyl or cycloalkyl.

* * * * *